(12) United States Patent
Vogel

(10) Patent No.: US 8,220,585 B2
(45) Date of Patent: Jul. 17, 2012

(54) NON-ELECTRONIC HEARING AID

(76) Inventor: Barry Vogel, Ukiah, CA (US)

(*) Notice: Subject to any disclaimer, the term of this patent is extended or adjusted under 35 U.S.C. 154(b) by 0 days.

(21) Appl. No.: 12/932,862

(22) Filed: Mar. 7, 2011

(65) Prior Publication Data

US 2012/0111659 A1 May 10, 2012

Related U.S. Application Data

(63) Continuation-in-part of application No. 12/927,100, filed on Nov. 8, 2010.

(51) Int. Cl.
H04R 25/00 (2006.01)
(52) U.S. Cl. ........................ 181/133; 181/136
(58) Field of Classification Search .................. 181/136; D24/174, 175
See application file for complete search history.

(56) References Cited

U.S. PATENT DOCUMENTS

| | | | | |
|---|---|---|---|---|
| 3,618,698 A | * | 11/1971 | McCabe et al. | 181/136 |
| 3,658,150 A | * | 4/1972 | Turner | 181/136 |
| 3,938,616 A | * | 2/1976 | Brownfield | 181/136 |
| D244,467 S | * | 5/1977 | Aquilino | D24/175 |
| D266,945 S | * | 11/1982 | Greenberg | D24/175 |
| 4,421,199 A | * | 12/1983 | Vrana | 181/136 |
| D278,431 S | * | 4/1985 | Beard | D14/205 |
| 4,574,912 A | * | 3/1986 | Fuss et al. | 181/129 |
| D286,873 S | * | 11/1986 | Ikeda | D24/175 |
| D292,916 S | * | 11/1987 | Ikeda | D14/205 |
| 4,768,613 A | * | 9/1988 | Brown | 181/136 |
| 4,771,859 A | * | 9/1988 | Breland | 181/136 |
| 4,890,688 A | * | 1/1990 | Baker | 181/136 |
| D310,530 S | * | 9/1990 | McGuire | D14/205 |
| 4,997,056 A | * | 3/1991 | Riley | 181/136 |
| 5,020,629 A | * | 6/1991 | Edmundson et al. | 181/136 |
| 5,060,850 A | * | 10/1991 | Weaver | 229/117.06 |
| D322,070 S | * | 12/1991 | Kitch | D14/205 |
| 5,189,265 A | * | 2/1993 | Tilkens | 181/133 |
| D341,885 S | * | 11/1993 | Hara | D24/175 |
| 5,345,512 A | * | 9/1994 | Lee | 381/377 |
| 5,696,356 A | * | 12/1997 | Dudley et al. | 181/136 |
| D397,118 S | * | 8/1998 | Keating | D14/221 |
| 5,965,850 A | * | 10/1999 | Fraser | 181/129 |
| 6,082,486 A | * | 7/2000 | Lee | 181/136 |
| 6,229,901 B1 | * | 5/2001 | Mickelson et al. | 381/371 |
| 6,237,714 B1 | * | 5/2001 | Lee | 181/136 |
| 6,571,907 B2 | * | 6/2003 | Jennings | 181/136 |
| 2005/0178610 A1 | * | 8/2005 | Broersma | 181/129 |
| 2009/0288775 A1 | * | 11/2009 | Iwasaki | 156/443 |

* cited by examiner

*Primary Examiner* — Jeremy Luks
(74) *Attorney, Agent, or Firm* — Donald Grant Kelly

(57) ABSTRACT

A non-electronic hearing aid with a left ear member and a right ear member. The left and right ear members are made of flat sheet material. The sheet is die cut into the left and right members. The left member is a mirror image of the right member. The members each die cut to form a hand shaped pattern. The fingers of the pattern each have a locking tab and or a locking slot. The locking tab of one finger engages with the locking slot of the adjacent finger to form a cup shape. The palm portion of the hand shape has a C shaped portion cut out which is sized to fit over a person's ear. A slot running parallel to the central part of the C shaped portion facilitates a bend in the sheet to allow the cup shape that is ninety degrees to the user's ear.

10 Claims, 12 Drawing Sheets

NON-ELECTRONIC HEARING AID

CROSS REFERENCE TO RELATED APPLICATIONS

This application is a Continuation-in-Part of Applicant's prior non-provisional patent application Ser. No. 12/927,100 filed Nov. 08, 2010. All benefits of the priority date of said prior application are hereby claimed under 35 USC 120.

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of hearing aids and more specifically to a non-electronic hearing aid.

Almost everyone has had the experience of putting one's hands up to one's ears in a cup shape to help direct sound into the ears. This is a natural response to helping one to a gather and amplify the sound entering one's ears in a non-electronic manner. To help facilitate hearing without the necessity of putting one's hands up to one's ears, it would be logical to manufacture a cup shape that mimics the shape of a person's cupped hand and to fasten that cup shape to the outside of each ear by means of a resilient band or other obvious method. In fact, a number of inventors have proposed just such a design and can be seen in their patents:
U.S. Pat. No. 1,708,257
U.S. Pat. No. 2,537,201
U.S. Pat. No. 3,938,616
U.S. Pat. No. 4,768,613
U.S. Pat. No. 4,997,056
U.S. Pat. No. 5,965,850
Even though the prior designs cited above do help to direct and amplify sound in a non-electronic manner, they have several deficiencies.

First, the examples sited above are all made by plastic injection molding or other plastic manufacturing process. The manufactured cost of an injection molded plastic product is such that the resulting product would not be considered a disposable item and therefore can not be used in a single use event.

Second, the contoured nature of the cup shapes shown in the above sited patents means that the devices sited would take up significant room for packaging purposes and would also be bulky when put in a person's purse or pocket and would therefore make it difficult to take them to a remote location such as a concert.

Third, the contoured shapes of the designs sited above make it difficult to print advertising slogans or logos on the cup shapes.

Paul Edmundson, in his patent U.S. Pat. No. 5,020,629 discloses a listening enhancement device that is made of die cut sheet material that is folded and snapped into place to form a shape that helps reflect sound into a person's ear. However, the Edmundson device does not effectively direct sound into the user's ear for several reasons. First, by the nature of the design, sound can be trapped between the sound reflective surface and the back of the user's ear. Second, Edmundson is calling for the use of a soft material to make the reflective surface. Experiments show that a hard flexible reflective surface is more effective in bouncing sound waves into the user's ear. Finally, although provision is made for some adjustment of the reflective surface by which snaps are used, the resulting reflective surface is not easily adjustable to more than two or three discrete positions.

BRIEF SUMMARY OF THE INVENTION

The primary object of the invention is to provide a non-electronic hearing aid that simulates the action of a person putting his hands up behind ones ears to help direct sound waves into ones ears.

Another object of the invention is to provide a non-electronic hearing aid that remains in close proximity to the back portions of the user's ear.

Still another object of the invention is to provide a non-electronic hearing aid whose sound reflective surface can be easily adjustable to a variety of parabolic shapes.

Another object of the invention is to provide a non-electronic hearing aid that enhances the range of frequency that the user can hear compared to when not wearing the invention.

Another object of the invention is to provide a non-electronic hearing aid that is held in its use position by only one tab and slot connector.

Another object of the invention is to provide a non-electronic hearing aid that is inexpensive to manufacture so as to be disposable if so desired.

Another object of the invention is to provide a non-electronic hearing aid that is die cut from a flat sheet of printable material.

A further object of the invention is to provide a non-electronic hearing aid that can be used for ad specialty purposes.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a non-electronic hearing aid comprising: a left ear member, a right ear member, said left and right ear members made of hard flat resilient sheet material, said flat resilient sheet material die cut into said left and right members, said left die cut member a mirror image of said right die cut member, said die cut members each cut folded and held in place by a single locking tab and slot, form a parabolic shape, said parabolic shape having a C shaped portion cut out, said C shaped portion sized to fit over a person's ear, and a score running parallel to the central part of said C shaped portion that facilitates a bend of said flat sheet material to allow said cup shape to be in close proximity to the rear of the user's ear.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
FIG. 1 is a perspective view of a person wearing the present invention.
Figure 2:
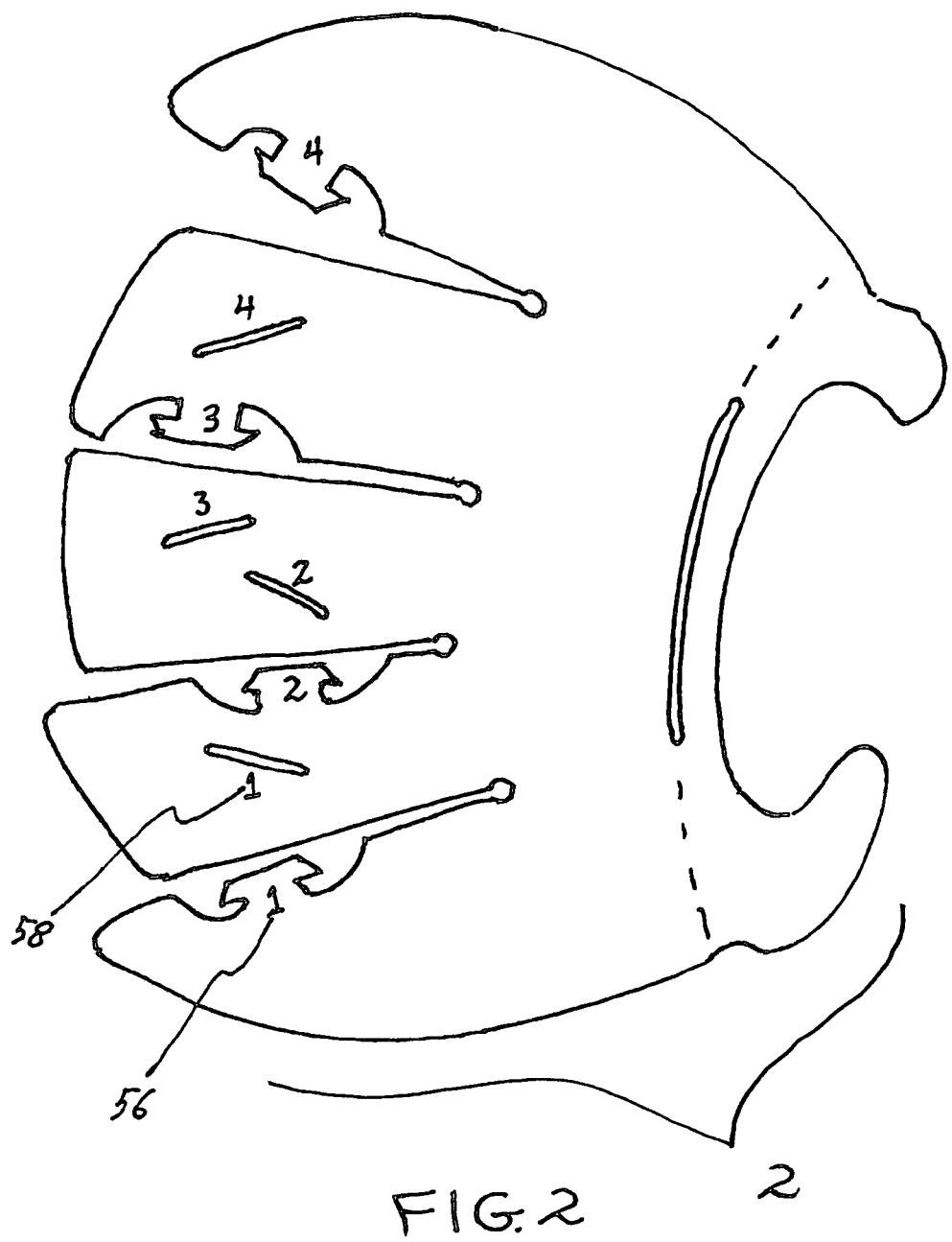
FIG. 2 is a plan view of the left ear member of the present invention.
Figure 3:
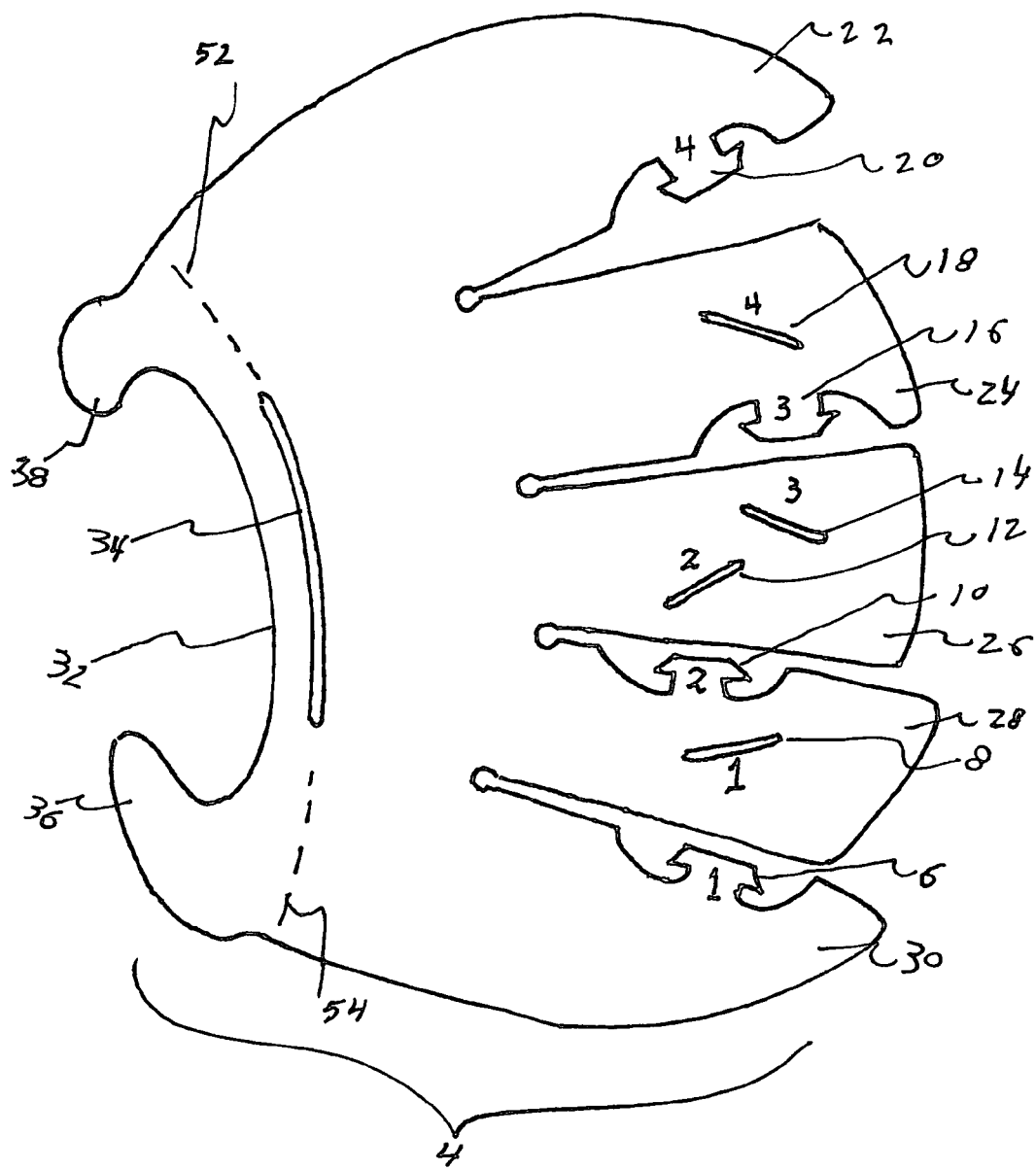
FIG. 3 is a plan view of the right ear member of the present invention.
Figure 4:
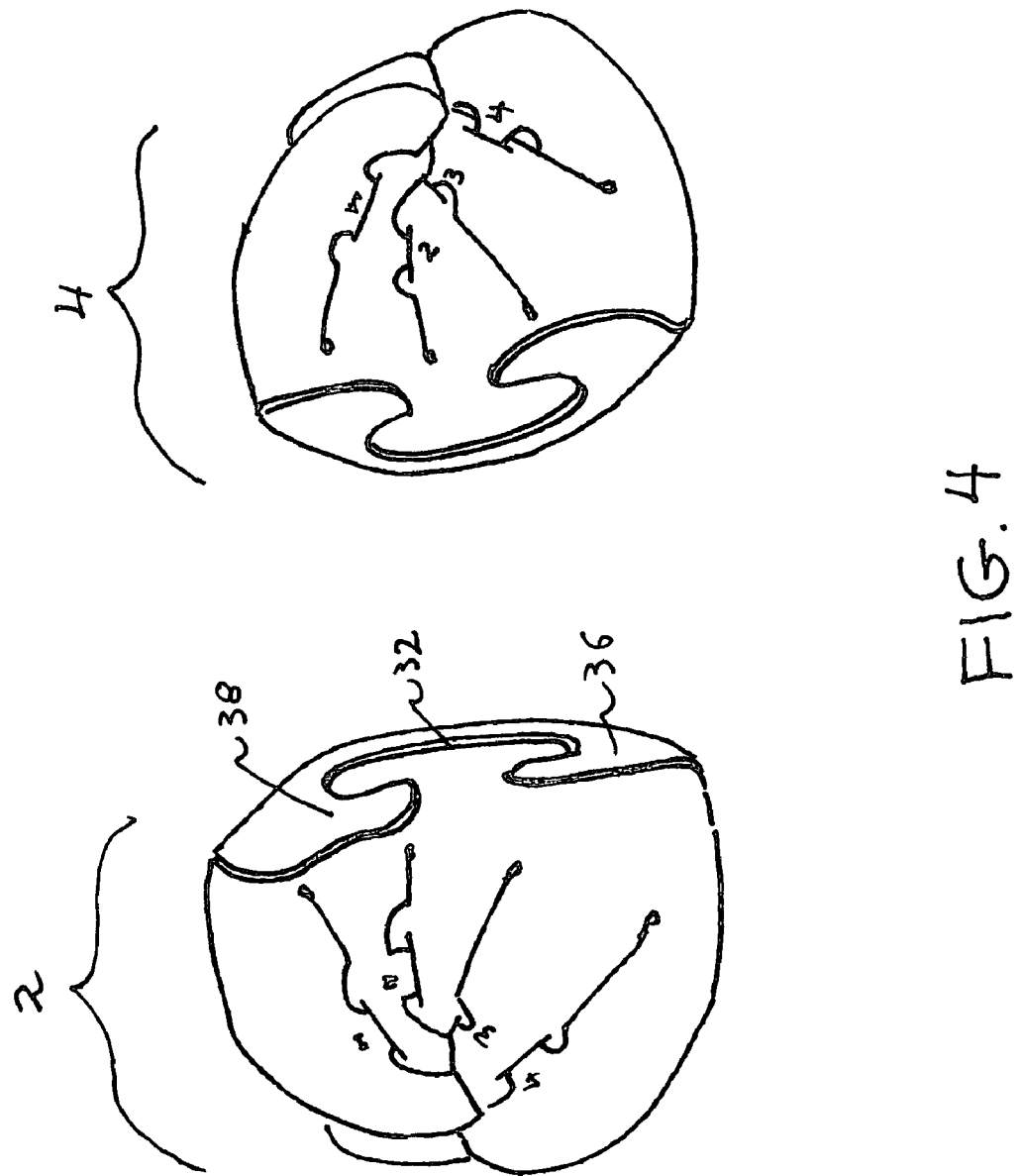
FIG. 4 is a perspective view of the left and right ear in the cup shape position.
Figure 6:
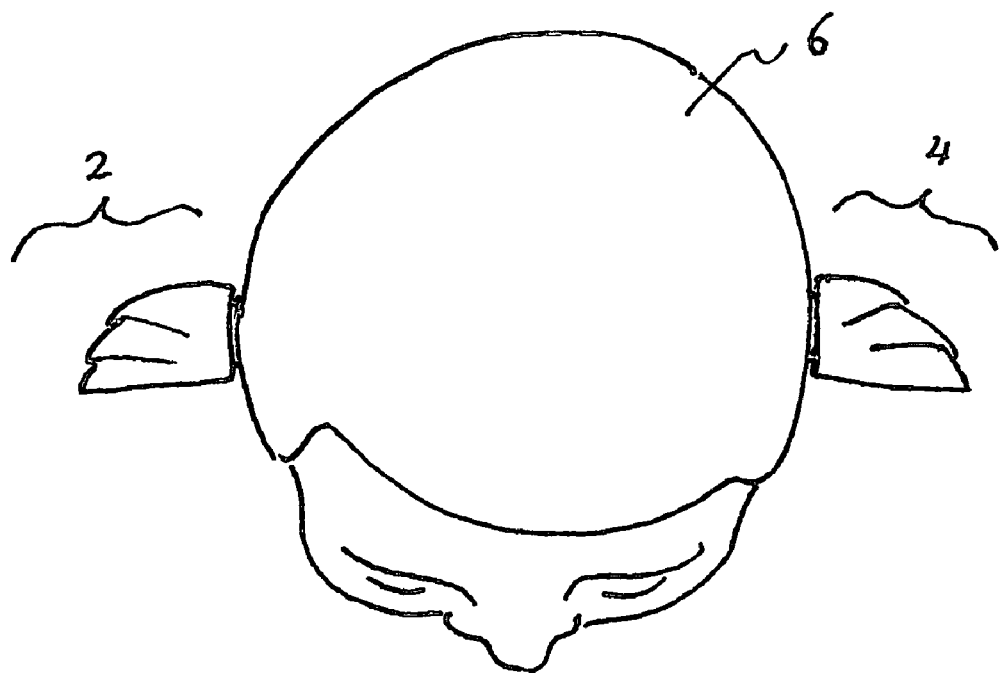
FIG. 6 is a top view of a person wearing the present invention.

Referring now to FIG. 1 we see a front view of a person 6 wearing a first embodiment of the non-electronic hearing aid of the present invention which consists of a left ear member 2 and a right ear member 4 that are approximately cup shaped and hook onto the user's ears via a C shaped cutout 32 shown in FIG. 3. The invention approximates the natural action of a person putting his hands up to his ears in a cupped position in order to catch more sound waves and direct them into his or her ears for the purpose of hearing more clearly, or hearing distant sounds more distinctly. Ear member 2 and ear member 4 are mirror images of each other. FIG. 6 shows a top view of the person 6 wearing the ear members 2, 4. The radial, sound gathering shape of the members can be clearly seen:

Figure two and three show the left 2 and right 4 ear members in the flattened position. The members 2, 4 are die cut from resilient sheet material such as heavy weight paper, thin plastic to approximately form a hand shape. For a less obtrusive appearance, the members 2, 4 can be die cut from transparent sheet material such as vinyl or polycarbonate. The cup shape of the members 2, 4 are created when the user inserts tabs 6, 10, 16, 20 into slots 8, 12, 14, 18. In this way, the fingers 30, 28, 26, 24, 22 overlap each other and gather the sheet material to form the desired cup shape as shown in FIG. 4.

A C shaped cutout 32 is die cut into the palm portion of the die cut hand shape for fastening to the user's ear. The resulting hook members 36, 38 hook over and under the user's ear to hold the members 2, 4 in the proper location on the user's head. A curved slot 34 running parallel to the central portion of the C shaped cutout provides a bend line for the user to bend the finger portion of the die cut hand shape into a ninety degree orientation with respect to the C shaped cutout. The dotted lines 52, 54 are printed onto the die cut sheet to instruct the user where to make the ninety degree bend. Additionally, indices 56, 58 are printed on each tab and slot to instruct the user how to insert each tab into each corresponding slot.

Figure 5:
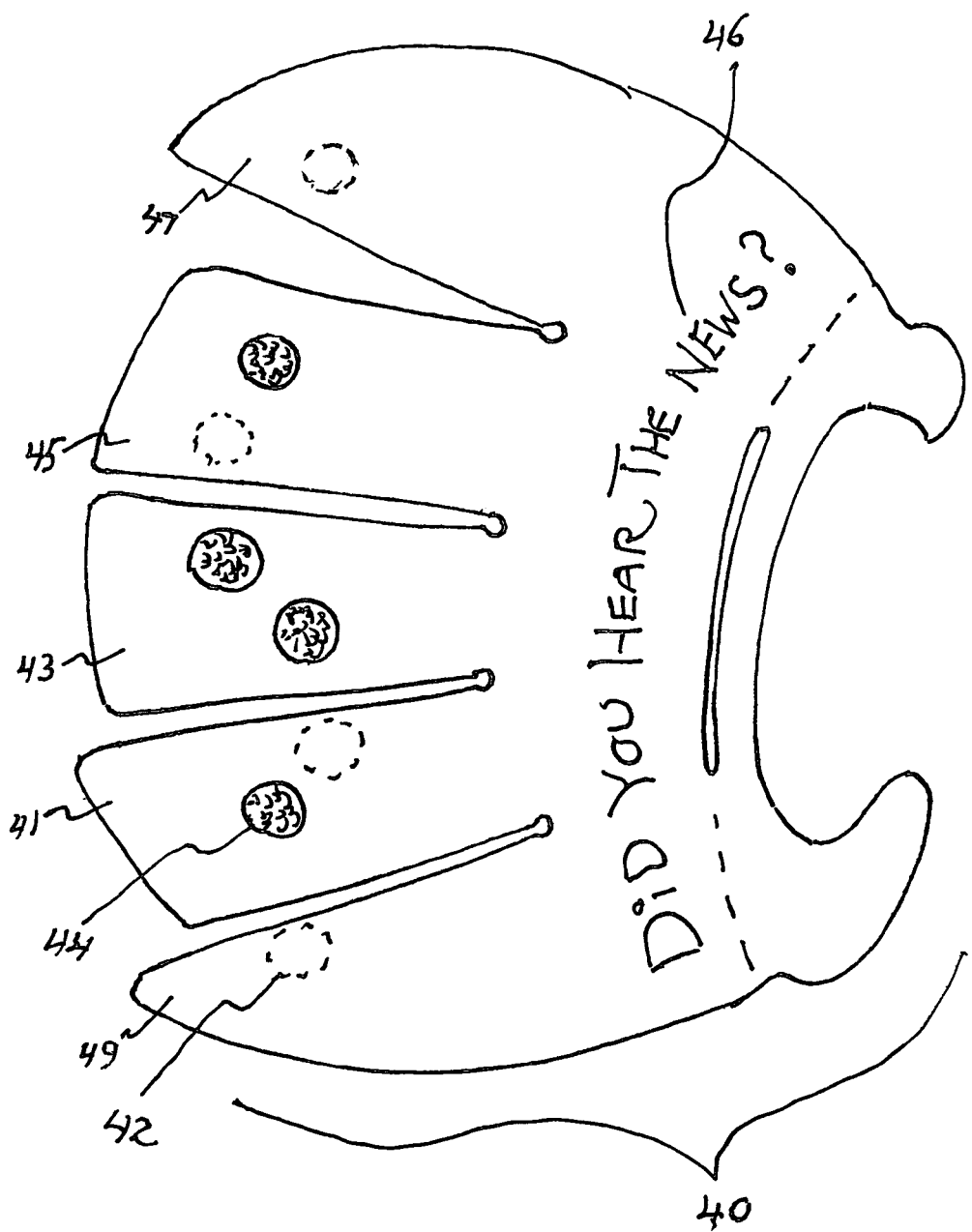
FIG. 5 is a plan view of an alternate embodiment of the invention.

Because the die cut ear members 2, 4 are so inexpensive to manufacture and because the die cut sheets start out in a flat position, they can be easily printed on 46, as shown in FIG. 5 and can be a disposable product to be discarded after one use.

In a second embodiment, shown in FIG. 5, hook 44 and loop 42 fasteners replace the tabs and slots of the first embodiment described above. The hook portions 44 are on the top side of fingers 41, 43, 45 and the loop portions 42 shown by dotted lines are on the underside of fingers 49, 41, 54, and 47. The hook portions 44 are attached to the loop portions 42 by the user to form the cup shaped ear members as described above. The hook and loop version of the invention allows the user to quickly and easily transform the die cut hand shape from the flat position to the cupped position and back again for compact storage and re use. Other standard fastening methods may also be used.

Figure 7:
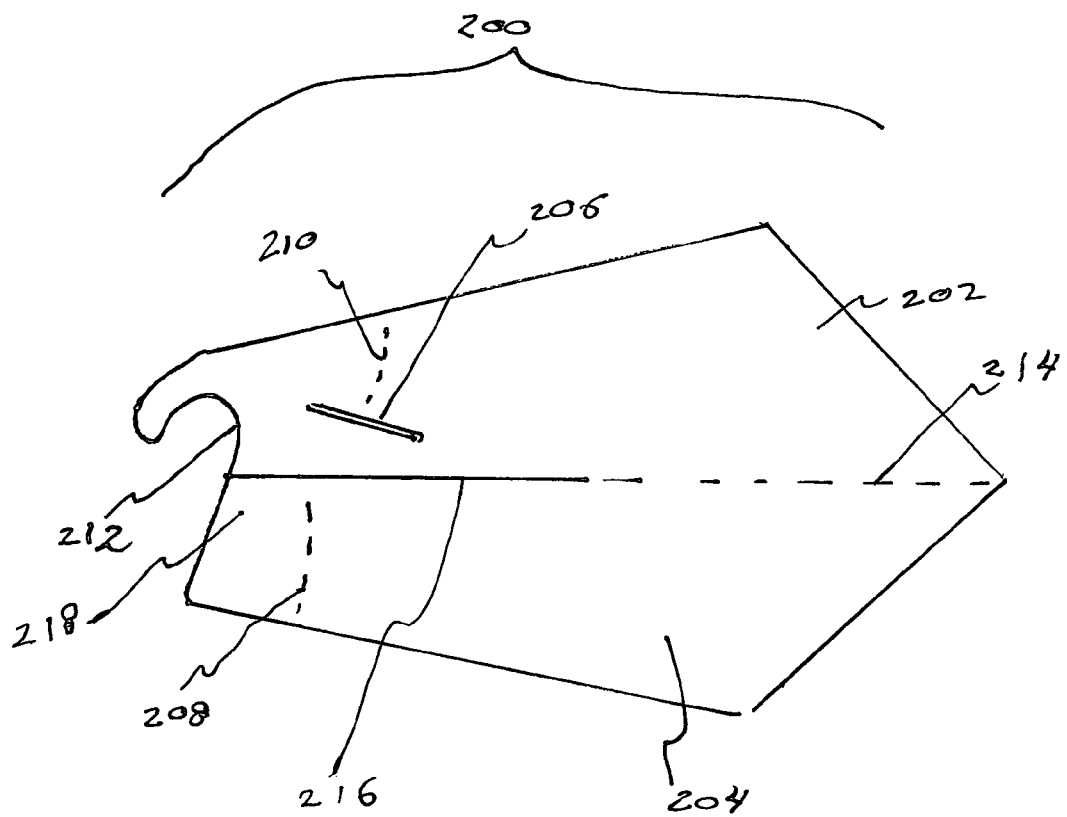
FIG. 7 is an alternate embodiment of the invention in the flat position.
Figure 8:
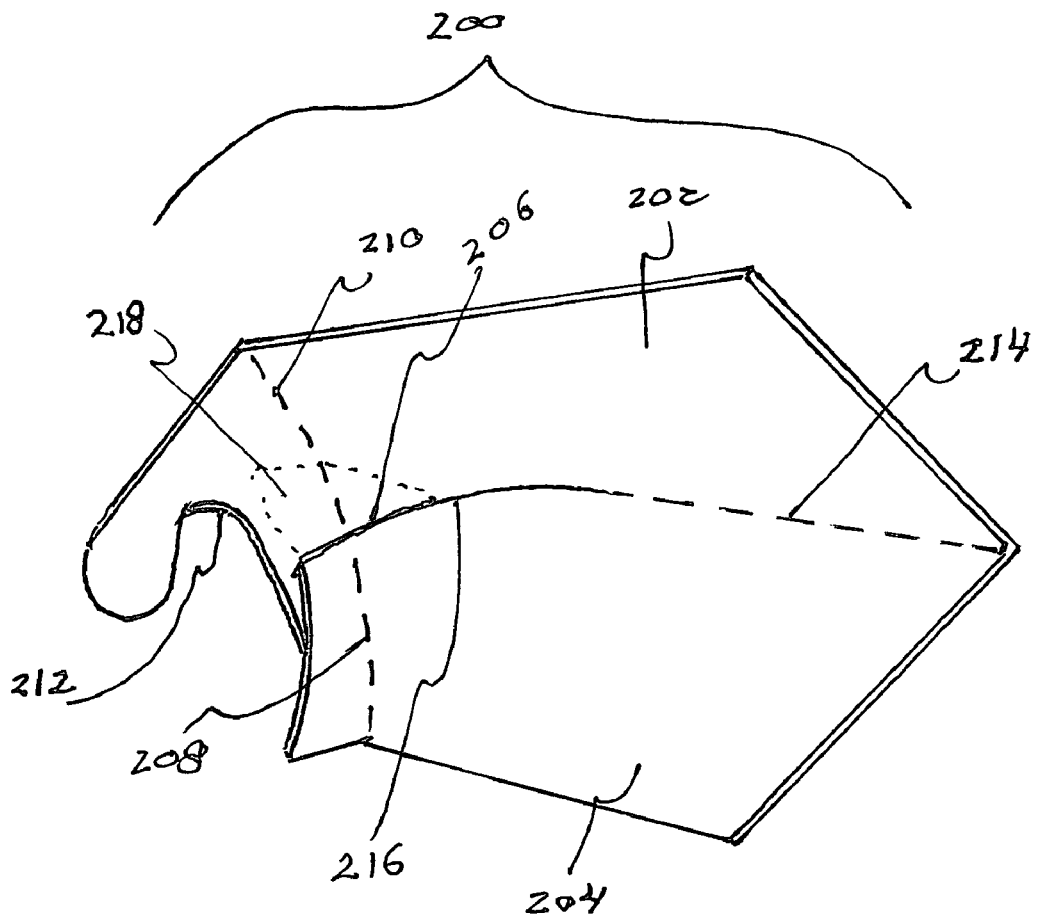
FIG. 8 is the alternate embodiment of the invention in the assembled position.

A third embodiment 200 can be seen in its flat form in FIG. 7. This is a simpler version than the one previously described however it still uses the novel principle of die cutting a shape from a flat flexible material, and bending the sheet and inserting one tab portion of the sheet into a slot on another portion of the sheet, creating a half funnel shape to direct sound into a person's ear. Referring back to FIG. 7, the flat, approximately rectilinear sheet 200 includes two main portions 202, 204, a main slit 216 and a smaller slit 206. The dotted lines 214, 208, 210 are printed onto the sheet and indicate fold lines. the J shaped portion 212 helps attach the device to the user's ear. FIG. 8 shows the same sheet 200 in the folded position where the sheet 200 has been folded along the dotted lines 214, 208, 210. and the tip 218 of portion 202, shown as a dotted line, has been inserted into slit 206. This folded shape forms a funnel that can direct sound into a person's ear.

Figure 9:
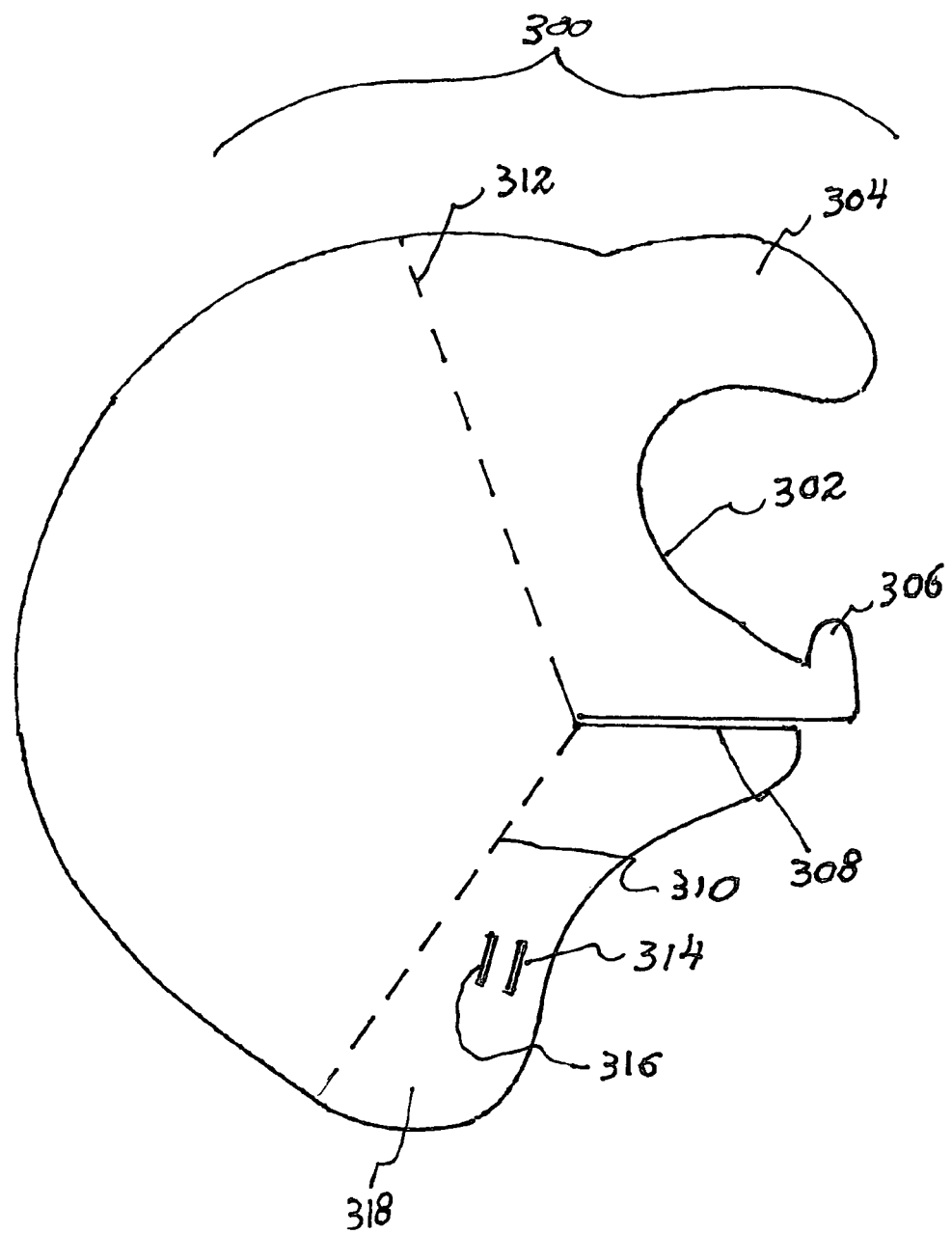
FIG. 9 is a flat plan view of a second alternate embodiment of the invention.
Figure 10:
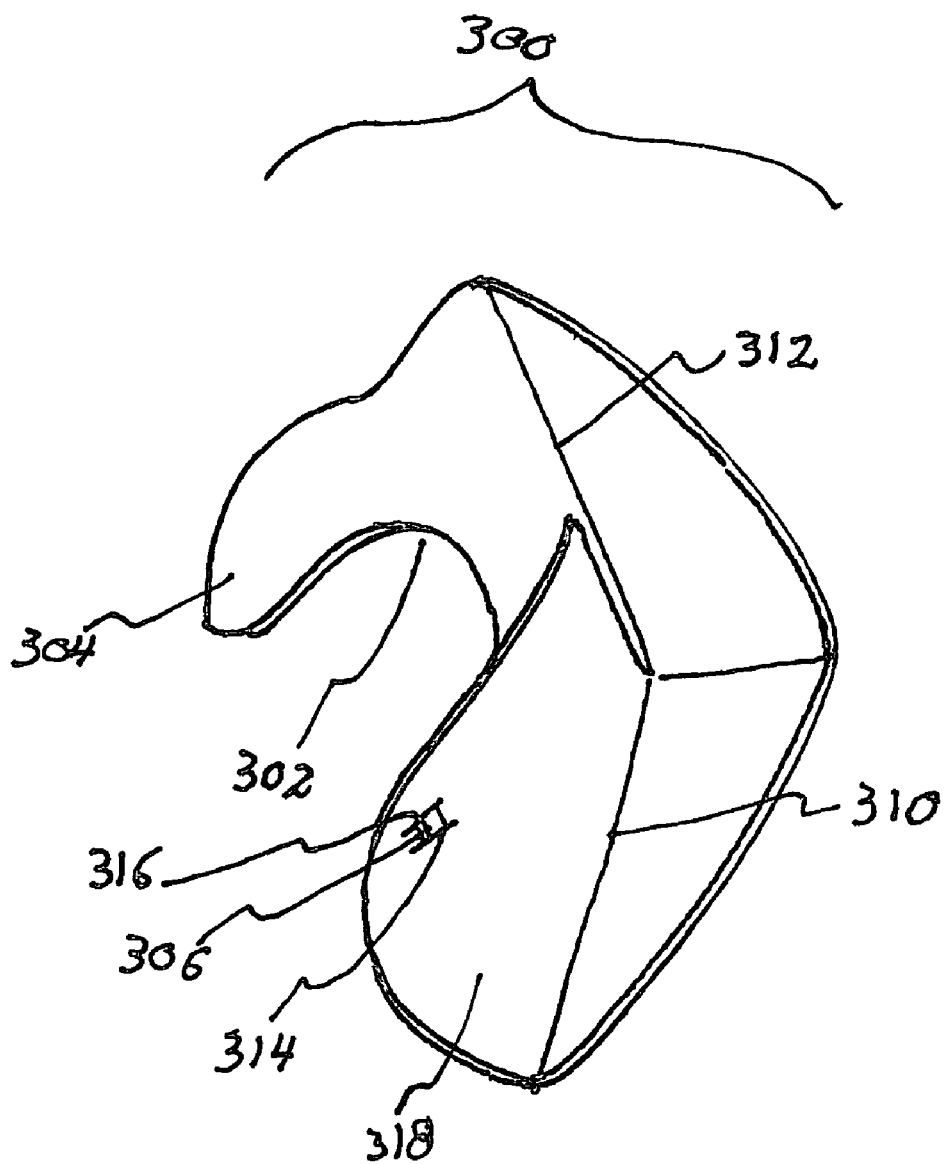
FIG. 10 is a front view of the folded version of the second alternate embodiment of the invention, ready for use.
Figure 11:
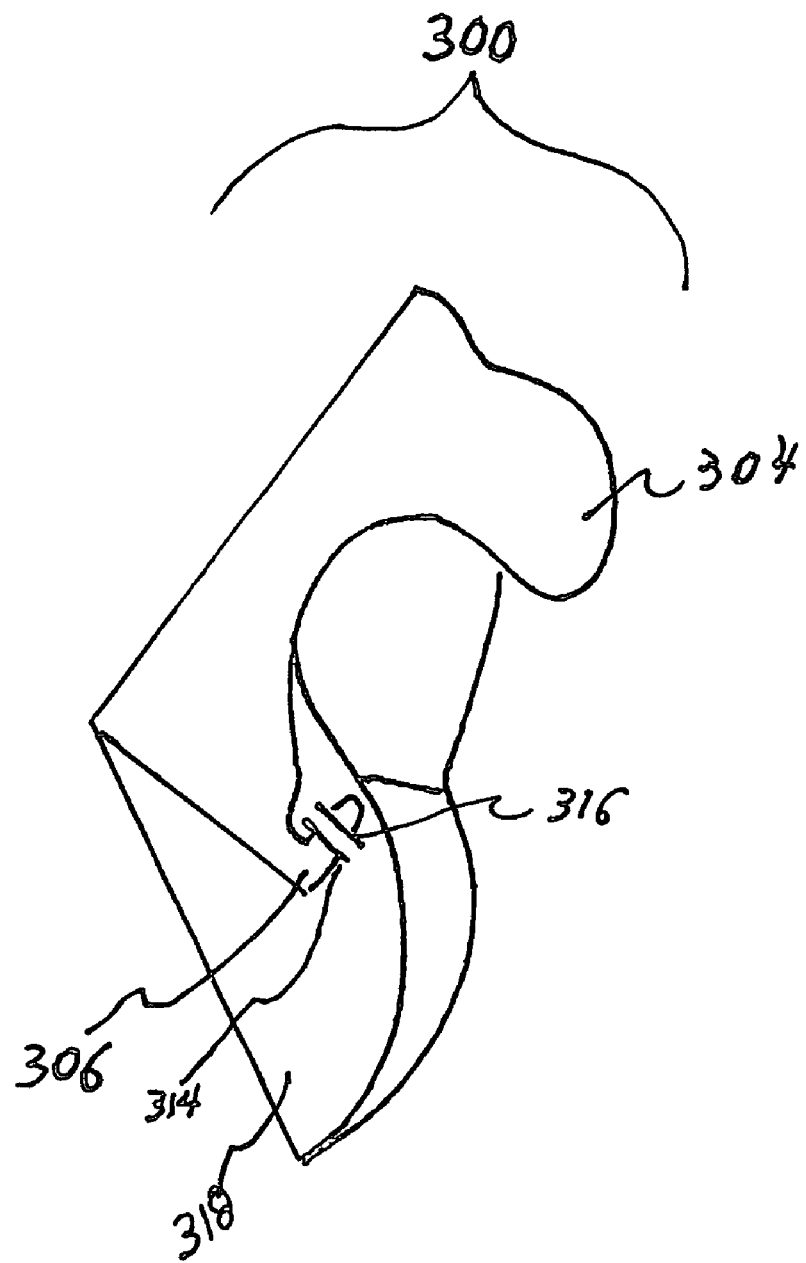
FIG. 11 is a rear view of the folded version of the second alternate embodiment of the invention, ready for use.
Figure 12:
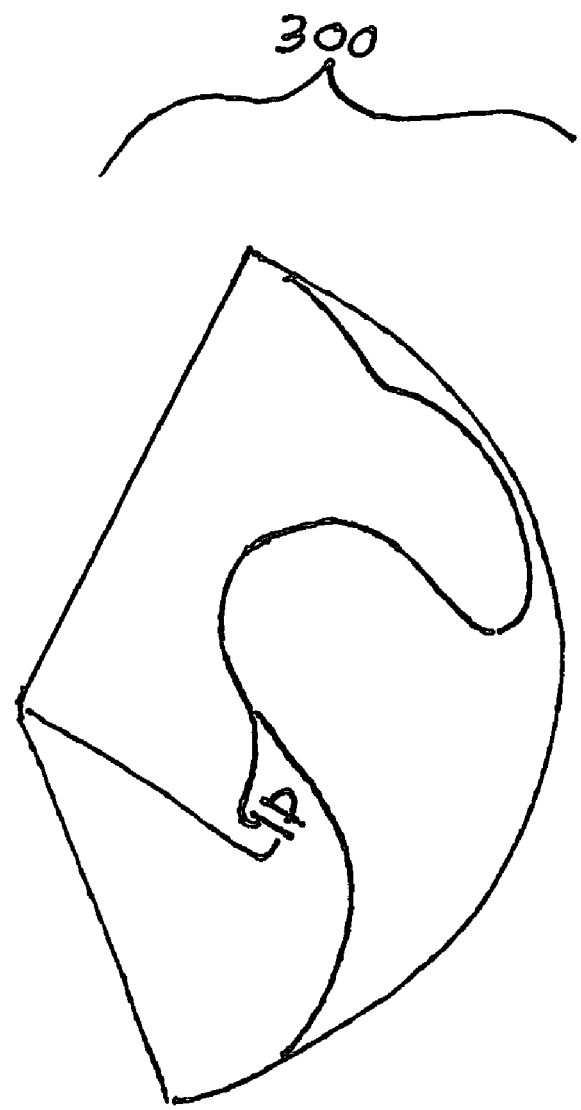
FIG. 12 is a flat folded view of the second embodiment of the invention, ready for storage in a pocket or purse.

FIG. 9 shows a flat plan view of another embodiment of the hearing aid device 300 shown here in its unfolded or collapsed (flattened) condition. As in the previous embodiments, the present embodiment is made of a single sheet of flexible and die cuttable substrate material such as heavy paper or thin plastic. As depicted in FIG. 9, the collapsible hearing aid device 300 presents three panel portions including a first sound capturing panel portion 320 with a generally parabolic outer periphery. This sound capturing panel portion is shown as defined between intersecting first and second substantially linear edges (or scored folding points) 312, 310. The first panel 320 shares a linear edge 312 with a second substrate portion 304. Second substrate portion 304 further has a second edge of general C shape (as detailed below) with a first terminal end to be fitted over a user's ear. A second terminal end of said second portion 304 includes a first connector part (e.g., tab) 306 for maintaining device 300 in folded condition. A third substrate panel portion 318 is separated by slit 308 from second portion 304, but shares a second linear edge (or scored folding points) 310 with said first panel portion 320 and has a second connector part (e.g., slots 314, 316) mating with connector part 306 to serve as the sole fastener (314, 316, 318) maintaining said device 300 in its folded, operative condition. Dotted lines 310, 312 indicate folding points which can be folded to create a sound amplifying and capturing device 300. Slit 308 allows panels 302 and 318 to overlap each other to form the three dimensional sound catching and amplifying shape as shown in the outward perspective view shown in FIG. 10. The device 300 shown in FIG. 10 is a perspective view and is in the folded, ready to use position. Panel portion 304 of the single sheet is cut to form a C shape with its ear engaging hook surface that fits over the user's ear. The design of the completed parabolic shape also fits in close proximity to the back of the user's ear, similar to the view of the first embodiment of the invention shown in the top view in FIG. 6, so that sound waves cannot be trapped between the sound reflecting surface 320 and the back of the user's ear. Therefore, no reverberation can occur behind the user's ear. Tab (connector part) 306 is designed to fit into corresponding connector parts in the form of die cut slits 314, 316 to hold the assembly together for use. The user may also decide to tape the overlapping panel portions 318, 304 together for permanent attachment. FIG. 11 shows the hearing aid device 300 in its folded, ready to use form as seen from the inside view. Sheet material panel portions 304 and 318 are meant to go against the user's head yet panel portion 304 can be placed in very close proximity to the back of the user's ear. Slits 314 and 316 can be clearly seen retaining tab 306. The user can easily adjust the curve of the sound reflective surface 320 by physically bending it to be more or less parabolic. The resulting reflective surface effectively directs all sound waves to the vicinity of the user's ear. Experiments show that the parabolic shape formed by the preferred embodiment 300 enhances the range of frequency, both on the upper range and the lower range, that the user can detect. Additionally, the angle of the parabolic surface 320 is between forty-five degrees and ninety degrees from the user's ear, as shown in the first embodiment of the invention in the to view of FIG. 6. Audiologist agrees that this ideal angle range for bouncing sound into the ear. FIG. 12 shows the preferred embodiment of the invention 300 in a folded and flattened position, ready for storage in a pocket or purse. The width of the folded flat design 300 is sized to allow the device 300 to easily fit within a standard shirt pocket.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A non-electronic hearing aid foldable between folded and collapsed condition and comprising a resilient sheet material substrate defined as having at least three interconnected, inter-foldable panel portions including:
   a first substrate panel portion having a flexible sound capturing surface with a generally parabolic outer peripheral edge, said first panel portion structurally defined by said outer peripheral edge and its intersecting first and second substantially linear panel edges;
   a second substrate panel portion sharing said first linear edge with said first panel portion, and having a second edge configured in a general c-shape with generally opposed terminal ends for fitting about a user's ear so as to retain said second substrate panel closely adjacent said user's head;
      a first of said terminal ends comprising an ear-engaging hook by which said hearing aid is suspended for use;
      a second of said terminal ends further defined as including a first connector part of a single fastener for securing said resilient sheet material substrate in a folded position;
   a third substrate panel portion is separated by a slit from said second substrate panel portion but shares said second linear edge with said first panel portion and includes a second connector part configured to mate with said first connector part of said single fastener for securing said resilient sheet material substrate in a folded position;
   said first and second substrate panel portions, in folded condition, interconnect at said first linear edge at an included angle of between 45 and 90 degrees, while said second and third substrate portions overlap one another to form a three-dimensional sound catching shape;
whereby said hearing aid in its folded condition suspends from an upper edge of the user's ear and fits in close proximity to a back portion thereof due to the included angle of said first and second substrate portions such that sound waves cannot be trapped between the flexible sound capturing surface and the back of the user's ear.

2. The foldable hearing aid set forth in claim 1 wherein said resilient substrate is a single continuous sheet of thin plastic material.

3. The foldable hearing aid of claim 2 wherein said thin plastic material is transparent.

4. The foldable hearing aid set forth in claim 1 wherein said substrate is a single continuous sheet of heavy paper.

5. The foldable hearing aid set forth in claim 1 wherein said first and second connector parts comprise a mating fastener.

6. The foldable hearing aid set forth in claim 5 wherein said mating fastener is a tab and slot connector.

7. The foldable hearing aid set forth in claim 6 wherein said tab and slot connector is the sole fastener for securing said resilient sheet material substrate in a folded position.

8. The foldable hearing aid set forth in claim 1 wherein said sound capturing surface is adjustable to a variety of parabolic shapes.

9. The foldable hearing aid set forth in claim 1 wherein said linear panel edges are defined as folding points.

10. The folding hearing aid set forth in claim 9 wherein said folding points are defined by score lines.

* * * * *